(12) United States Patent
Makarov et al.

(10) Patent No.: US 10,551,449 B2
(45) Date of Patent: Feb. 4, 2020

(54) WHOLE BODY NON-CONTACT ELECTRICAL STIMULATION DEVICE WITH VARIABLE PARAMETERS

(71) Applicant: Neva Electromagnetics, LLC, Yarmouth Port, MA (US)

(72) Inventors: Sergey N Makarov, Holden, MA (US); Gregory M Noetscher, Shrewsbury (UY); Viktor S Makarov, Holden, MA (US); Zhi-De Deng, Bathesda, MD (US)

(73) Assignee: Neva Electromagnetics, LLC, Yarmouth Port, MA (US)

( * ) Notice: Subject to any disclaimer, the term of this patent is extended or adjusted under 35 U.S.C. 154(b) by 0 days.

(21) Appl. No.: 15/868,038

(22) Filed: Jan. 11, 2018

(65) Prior Publication Data

US 2018/0196113 A1    Jul. 12, 2018

Related U.S. Application Data

(60) Provisional application No. 62/444,940, filed on Jan. 11, 2017.

(51) Int. Cl.
*G01R 33/34*    (2006.01)

(52) U.S. Cl.
CPC .............. *G01R 33/34076* (2013.01)

(58) Field of Classification Search
CPC ........ G01R 33/34076; A61N 1/40; A61B 5/05
USPC ......................................................... 324/318
See application file for complete search history.

(56) References Cited

U.S. PATENT DOCUMENTS

| 4,916,418 | A | 4/1990 | Rath |
| 5,041,790 | A * | 8/1991 | Tropp .............. G01R 33/34061 324/318 |
| 6,316,941 | B1 | 11/2001 | Fujita et al. |
| 6,608,480 | B1 * | 8/2003 | Weyers .............. G01R 33/3415 324/318 |
| 6,791,328 | B1 * | 9/2004 | Nabetani .......... G01R 33/34076 324/318 |
| 7,119,541 | B2 | 10/2006 | Barberi |
| 8,680,863 | B1 * | 3/2014 | Qian .................. G01R 33/3635 324/307 |

(Continued)

FOREIGN PATENT DOCUMENTS

| RU | 2344411 | 1/2009 |
| WO | 200456229 | 4/2004 |

OTHER PUBLICATIONS

Tadesse, Yonatan Abebe. The Electromagnetic Simulation of Birdcage Coils for MRI based on Finite Element Method. Diss. Youngstown State University, 2016. (Year: 2016).*

(Continued)

*Primary Examiner* — Christopher P McAndrew
(74) *Attorney, Agent, or Firm* — Moore, Ingram, Johnson & Steele, LLP

(57) ABSTRACT

The present invention relates to an electromagnetic device for non-contact injection of strong modulated (0-1000 Hz) electric fields with intensity of 1-2 volts per centimeter into a whole human body at the frequency band 100-500 kHz. The device of the present invention is a low-pass birdcage coil resonator with a very large number of rungs, with two inductively coupled loop feeds, and with a high quality factor of 300.

5 Claims, 2 Drawing Sheets

(56) References Cited

U.S. PATENT DOCUMENTS

| | | | | |
|---|---|---|---|---|
| 2004/0070398 | A1* | 4/2004 | Wong | G01R 33/34053 324/322 |
| 2006/0244453 | A1* | 11/2006 | Doty | G01R 33/34046 324/322 |
| 2010/0188086 | A1* | 7/2010 | Lazar | G01R 33/34076 324/318 |
| 2010/0253333 | A1* | 10/2010 | Zhai | G01R 33/3046 324/307 |
| 2011/0025329 | A1* | 2/2011 | Utturkar | G01R 33/3403 324/318 |
| 2012/0242338 | A1 | 9/2012 | Freytag | |
| 2012/0268132 | A1* | 10/2012 | Zhu | G01R 33/3642 324/322 |
| 2013/0015858 | A1* | 1/2013 | Ferrand | G01R 33/34076 324/322 |
| 2013/0271141 | A1 | 10/2013 | Zhang et al. | |
| 2013/0293232 | A1* | 11/2013 | Boskamp | G01R 33/422 324/318 |
| 2015/0276897 | A1* | 10/2015 | Leussler | G01R 33/34076 324/322 |
| 2017/0052235 | A1* | 2/2017 | Mohebbi | G01R 33/34007 |
| 2017/0089989 | A1* | 3/2017 | Findeklee | G01R 33/34007 |

OTHER PUBLICATIONS

Hayes et al. An efficient, highly homogeneous radiofrequency coil for whole-body NMR imaging at 1.5 T. J. Mag. Reson. 1985; 63: 622-628.

Hayes, "The development of the birdcage resonator: A historical perspective," NMR in Biomedicine, vol. 22, pp. 908-918, 2009.

Leary et al., Soft Magnetic Materials in High-Frequency, High-Power Conversion Applications. JOM (2012) 64: 772. doi:10.1007/s11837-012-0350-0.

4. "Soft ferrites and accessories data handbook," Ferroxcube International Holding B.V., Tech. Rep., 2013.

Hanson et al., Measurements and Performance Factor Comparisons of Magnetic Materials at High Frequency, 2015 Energy Conversion Congress and Exposition, pp. 5657-5666, Sep. 2015.

Rachael Parker & Michael Arasim, Low Loss 67 Material for High Frequency Power Applications, Fair-Rite Products Corporation, APEC 2016.

\* cited by examiner

WHOLE BODY NON-CONTACT ELECTRICAL STIMULATION DEVICE WITH VARIABLE PARAMETERS

CROSS-REFERENCE TO RELATED APPLICATIONS

This application claims benefit of U.S. Provisional Application 62/444,940, filed Jan. 11, 2017. The subject matter if that application is hereby included in its entirety.

FIELD OF THE INVENTION

The present invention relates to an electromagnetic device for non-contact injection of strong modulated electric fields into a whole human body at the frequency band 100-500 kHz.

BACKGROUND OF THE INVENTION

The conventional MRI (Magnetic Resonance Imaging) RF (Radio Frequency) coil or a birdcage resonator known from MRI instrumentation cannot be used in the frequency band 100-500 kHz since its quality factor Q, the "gain" of the resonator, becomes very low (less than one). As a result, the induced electric field in a body will be low too. To achieve high levels of the stimulation electric field, a birdcage coil resonator operating at a much lower carrier frequency of around 100-500 kHz is required. The carrier may then amplitude-modulated by any required base frequency in the range of 0-1000 Hz or by constructing pulsed excitation with a center frequency not to exceed 1000 Hz.

Accordingly, a resonator with a high field, up to 1-2 volts per centimeter, that operates at much lower than frequencies is required. The birdcage resonator of the present invention uses a very large number of rungs in excess of 100 while the conventional MRI resonator uses 8-16 rungs. It also uses inductively coupled feeds. These two factors allow achievement of a very high quality factor of 300 and high-fields of 1-2 volts per centimeter. Such a device may be used to modulate the field level with any signal including electroencephalographic signals from the brain to establish closed-loop feedback for the entire peripheral and/or nervous system. Other potential applications include treatment of chronic pain, oncological and psychiatric applications.

SUMMARY OF THE INVENTION

The present invention provides a resonant non-contact device, wherein the device creates strong variable electric fields in the human body in the frequency band 100-500 kHz. The device of the present invention comprises a modified birdcage coil or birdcage resonator. The generally cylindrical birdcage coil is further comprised of a pair of end rings, a plurality of generally parallel rungs or column elements bridging the end rings, a plurality of matching capacitors, and two inductively coupled loop feeds connected to a source with a 90 degrees phase shift.

In a preferred embodiment, the end rings are disposed in parallel planes along the coil axis and the parallel rungs interconnect the end rings. The end rings may be detachable to the parallel rungs. The plurality of parallel rungs are spaced generally equally about the end rings. In a preferred embodiment, the parallel rungs are comprised of a conductive material, preferably copper, and preferably thin-walled copper tubing.

In a further embodiment, each parallel rung is comprised of two rung portions with a capacitor located at the attachment point of the two rung portions. The capacitors are located distal to the end rings and, preferably, equidistant to each end ring. The capacitors are, preferably matching and in the nanofarad range used to tune the resonator to the desired frequency.

In a preferred embodiment, two inductively coupled loop feeds are disposed outside the parallel rungs proximally to the coil center. Each loop feed is shifted 90 degrees about the coil axis.

In a further embodiment, the birdcage coil of the present invention is driven through two inductively coupled feeds in quadrature by an amplifier, preferably a 3 kilowatt power amplifier.

In a further embodiment, the power amplifier includes amplitude modulation in the frequency band 0-1000 Hz.

DETAILED DESCRIPTION OF THE INVENTION

Figure 1A:
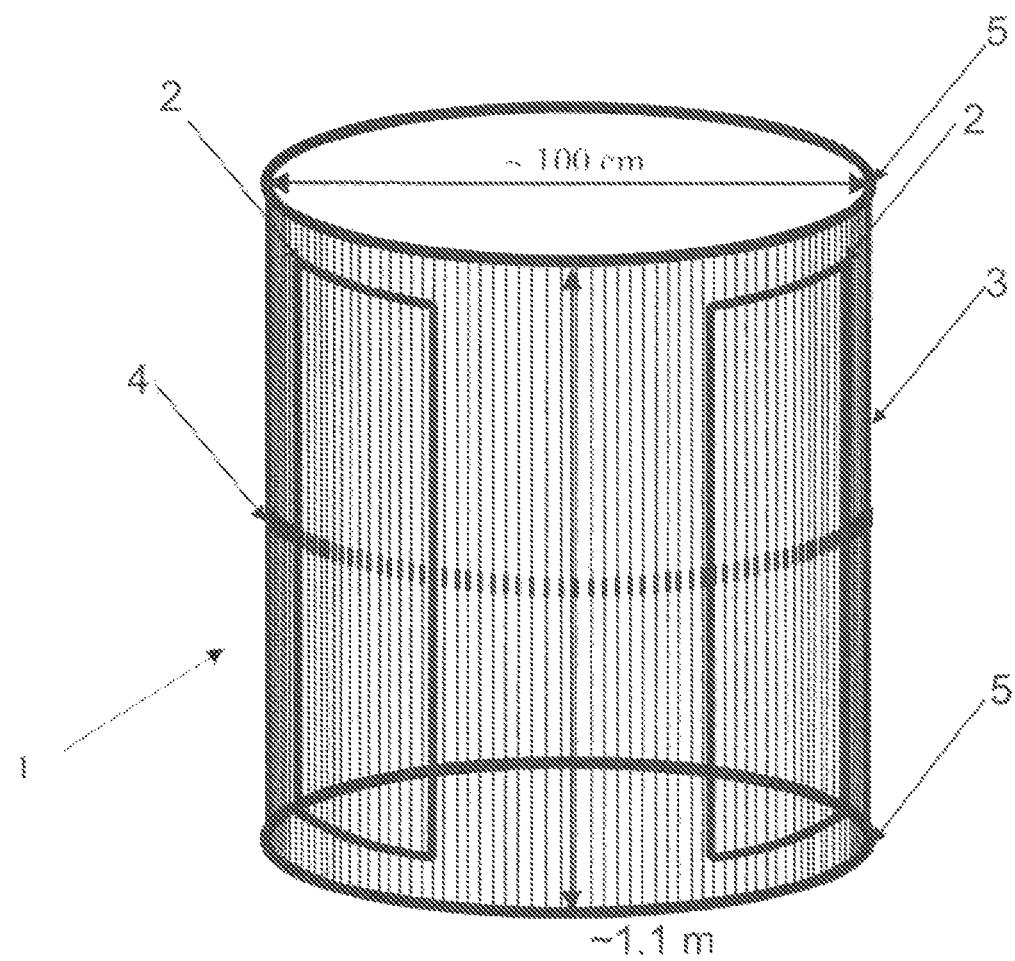
FIG. 1a is a schematic representation of a birdcage resonator of the present invention.

FIG. 1a shows a birdcage resonator 1 of the present invention. The resonator comprises end rings 5, capacitors 4, parallel rungs 3, and inductive loop feeds 2. The end rings 5 are disposed along parallel planes and are interconnected by the parallel rungs 3. Each parallel rung 3 is comprised of at least two leg portions 6. Capacitors 4 connect the rung portions 6 to form a parallel rung 3. Inductively coupled loop feeds 2 are placed parallel to rungs 3.

Figure 1B:
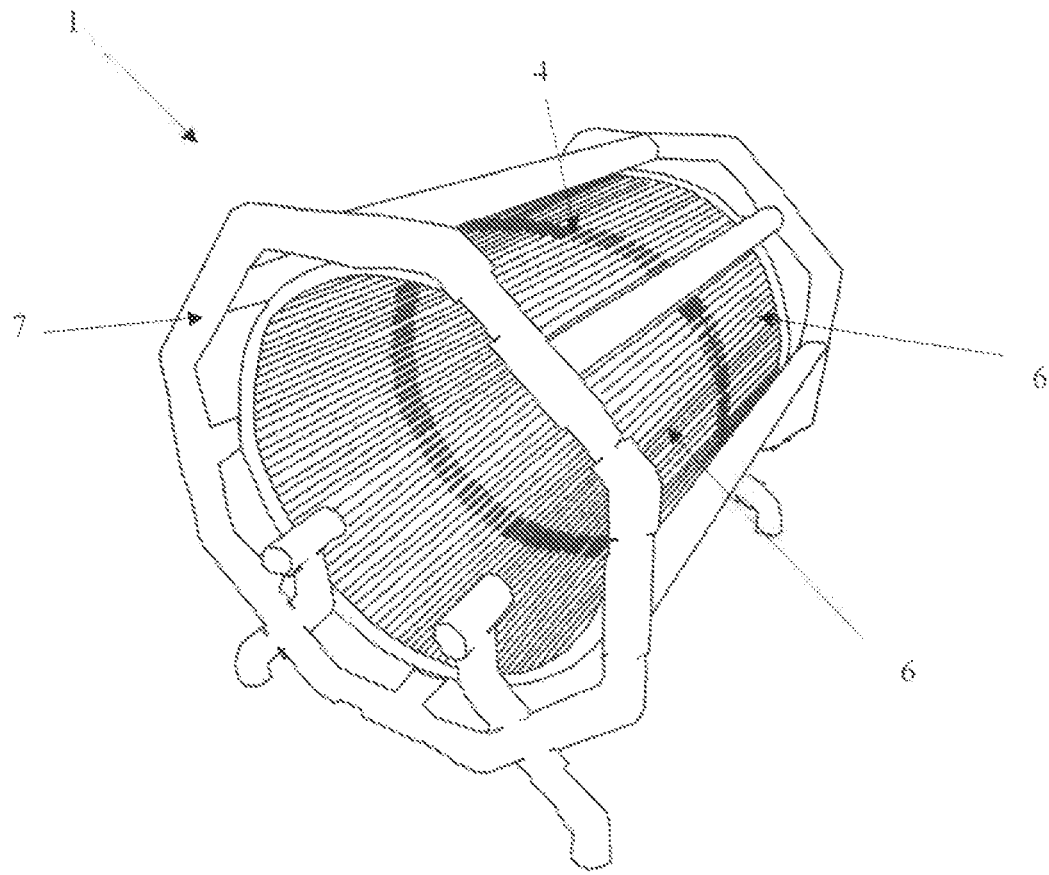
FIG. 1b is a schematic representation of a birdcage coil of the present invention.

FIG. 1b shows the birdcage resonator 1 supported by plastic frame 7. FIG. 1b further shows that each parallel rung 3 is comprised of at least two leg portions 6.

We claim:

1. A high-quality factor large-size low-frequency resonator at 100-500 kHz comprising:
   a pair of end rings;
   a plurality of rungs, wherein the plurality of rungs is in excess of 100 and bridge the end rings, and the plurality of rungs are generally parallel and spaced evenly about the end rings;
   a pair of non-contact inductive feeding loops for wireless power transfer to the resonator wherein the non-contact inductive feeding loops are placed parallel to the plurality of rungs.

2. The resonator of claim 1 wherein the plurality of rungs and the pair of end rings are comprised of thin-walled copper.

3. The resonator of claim 2 wherein the low-frequency electric field at 100-500 kHz in a human body within the resonator reaches and exceeds one volt per centimeter when driven by a 3 kilowatt power source.

4. The resonator of claim 3 wherein the low-frequency electric field at 100-500 kHz in a human body within the resonator may be modulated by any extremely low frequency from 0 to 1000 Hz.

5. The resonator of claim 1 wherein each of the plurality of rungs is further comprised of at least two leg portions that are connected by a capacitor.

* * * * *